United States Patent [19]

Sugahara

[11] Patent Number: 6,004,285
[45] Date of Patent: Dec. 21, 1999

[54] INJECTOR HEAD FOR MEDICAL USE

[75] Inventor: Tomio Sugahara, Osaka, Japan

[73] Assignee: Sugan Co., Ltd., Osaka, Japan

[21] Appl. No.: 08/985,220

[22] Filed: Dec. 4, 1997

[30] Foreign Application Priority Data

Dec. 6, 1996 [JP] Japan ................................. 8-327138

[51] Int. Cl.$^6$ ................................................. A61M 31/00
[52] U.S. Cl. ........................................... 604/67; 604/151
[58] Field of Search ............................... 604/65, 66, 67, 604/151, 152; 128/DIG. 12, DIG. 1

[56] References Cited

U.S. PATENT DOCUMENTS 3,701,345  10/1972  Heilman, et al. ..................... 604/66
4,006,736  2/1977   Kranys et al. ..................... 128/DIG. 1
4,695,271  9/1987   Goethel ............................. 128/DIG. 1

FOREIGN PATENT DOCUMENTS 94008647  4/1994  WIPO ..................................... 604/151

*Primary Examiner*—Jeffrey A. Smith
*Assistant Examiner*—Eduardo C. Robert
*Attorney, Agent, or Firm*—McDermott, Will & Emery

[57] ABSTRACT

An injector head for medical use is provided with a tilt sense circuit between a switch circuit and a body control unit for sensing a tilt of the injector head, converting a signal output from the switch circuit to a prescribed signal and outputting it to the body control unit. Accordingly, an injector head is provided which can be operated without care at the time of injection of contrast medium into a patient.

3 Claims, 4 Drawing Sheets

INJECTOR HEAD FOR MEDICAL USE

BACKGROUND OF THE INVENTION

1. Field of the Invention

The present invention relates to an injector head for medical use, and more particularly relates to improvement of the structure of the injector head for medical use.

2. Description of the Background Art

Various apparatuses for testing the function of the human body have been developed recently. One example is a circulatory organ x-ray diagnostic apparatus for diagnosing the function of the circulatory organ of the human body. With reference to FIG. 2, a general description of the circulatory organ x-ray diagnostic apparatus will be given.

A circulatory organ x-ray diagnostic apparatus 100 is provided with a rail 103 attached to a ceiling 101. An x-ray apparatus 102 which is movable freely in X and Y directions is attached to rail 103. A catheter table 104 for laying a patient 106 at a prescribed position is arranged at a prescribed position.

A side of catheter table 104 has a guide rail 108. Guide rail 108 has an equipment attached for performing the procedure necessary for the x-ray diagnosis for patient 106. In FIG. 2, for example, a support unit 200 is mounted on guide rail 108, and an injector head for medical use 112 for injecting contrast medium into patient 106 is attached to support unit 200 via a stanchion 114. By moving support unit 200 along guide rail 108 medical injector head 112 can be positioned at patient 106, and interference with any other apparatus can be avoided.

A syringe 10 into which the contrast medium is injected is attached to medical injector head 112. When the contrast medium is injected into patient 106 using medical injector head 112, medical injector head 112 is inclined downward such that an injection unit 10a of syringe 10 faces downward. Even if air bubbles enter syringe 10, injection of air bubbles into patient 106 can be prevented by arranging injection unit 10a of syringe 10 to face downward in order to collect the air bubbles in the rear end portion of syringe 10 as shown in FIG. 3A.

On the other hand, when the air bubbles entering syringe 10 are to be discharged or the contrast medium is to be sucked into syringe 10, medical injector head 112 is inclined upward such that injection unit 10a of syringe 10 faces upward as shown in FIG. 3B. The air bubbles entering syringe 10 at the time of the sucking can easily be discharged from injection unit 10a of syringe 10 to the outside after the injection.

Next with reference to FIG. 4, the mechanism of injector head for medical use 112 is described.

Medical injector head 112 includes a plunger 21 joined to a piston 20 provided in syringe 10. Rotation of a motor 30 is propagated to a ball screw 22, and plunger 21 can be moved forward and backward by ball screw 22.

Motor 30 is provided with a potentiometer 23 for sensing a position of plunger 21. A plunger position signal S3 output from potentiometer 23 is supplied to a body control unit 200.

A motor drive voltage S2 is output from body control unit 200 to motor 30. When an amount of injection of the contrast medium into a patient is input to a control panel 150, a corresponding signal is output from control panel 150 to body control unit 200, and motor drive voltage S2 is output from body control unit 200 to motor 30. At this time, plunger position signal S3 is supplied from potentiometer 23 to body control unit 200 as a feedback signal. Accordingly, the position of plunger 21 can be controlled correctly, and the contrast medium can be injected highly accurately into the patient.

Injector head for medical use 112 is further provided with an switch 50 for advancing and retracting plunger 21 by manual operation, as well as a manual knob 112b (see FIG. 3A). A variable forward/reverse switch is utilized as switch 50 which is capable of varying the speed in forward and backward movements by changing the position on the switch to be pressed.

A signal from switch 50 is output to a switch circuit 40 and a switch signal S100 is supplied to body control unit 200. Motor drive voltage S2 is thereafter output from body control unit 200 to motor 30.

When the contrast medium is injected into patient 106 by inclining medical injector head 112 downward as shown in FIG. 3A, sucking is performed slowly in order to check if a catheter is inserted into the blood vessel of patient 106. If the blood rises into the catheter, it means that the catheter has been surely inserted into the blood vessel.

In this case, if the contrast medium is sucked at higher speed, the blood flows backward into the catheter and enters syringe 10. An operator of injector head 112 such as a nurse or a medical technologist needs to operate switch 50 or manual knob 112b such that the piston is moved very carefully and slowly.

SUMMARY OF THE INVENTION

An object of the present invention is to provide an injector head for medical use which can be operated safely and easily without care at the time of injection of contrast medium into a patient.

An injector head for medical use according to the present invention includes: a piston drive apparatus for moving a piston provided in a syringe toward a front end and a rear end; a control apparatus for input/output of a prescribed control signal to/from the piston drive apparatus; and an operation apparatus for inputting a prescribed operation signal to the control apparatus in order to move the piston by manual operation. The injector head for medical use further includes a tilt sense apparatus for sensing a tilt of the injector head for medical use and outputting a sense signal based on the sensing to the control apparatus.

Preferably, a signal output from the operation apparatus is supplied to the tilt sense apparatus, and based on the signal, a sense signal is output from the tilt sense apparatus to the control apparatus.

A benefit derived from the provision of the tilt sense apparatus is as follows. If the medical injector head tilts upward, for example, a signal output from the operation apparatus is not converted. On the other hand, if the medical injector head tilts downward, the signal output from the operation apparatus is input to the tilt sense apparatus, and based on the input signal, a sense signal is output from the tilt sense apparatus to the control apparatus.

Accordingly, when the contrast medium is injected into a patient with the medical injector head tilted downward, the contrast medium can be sucked without much care in order to check if the catheter is surely inserted into the blood vessel of the patient.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
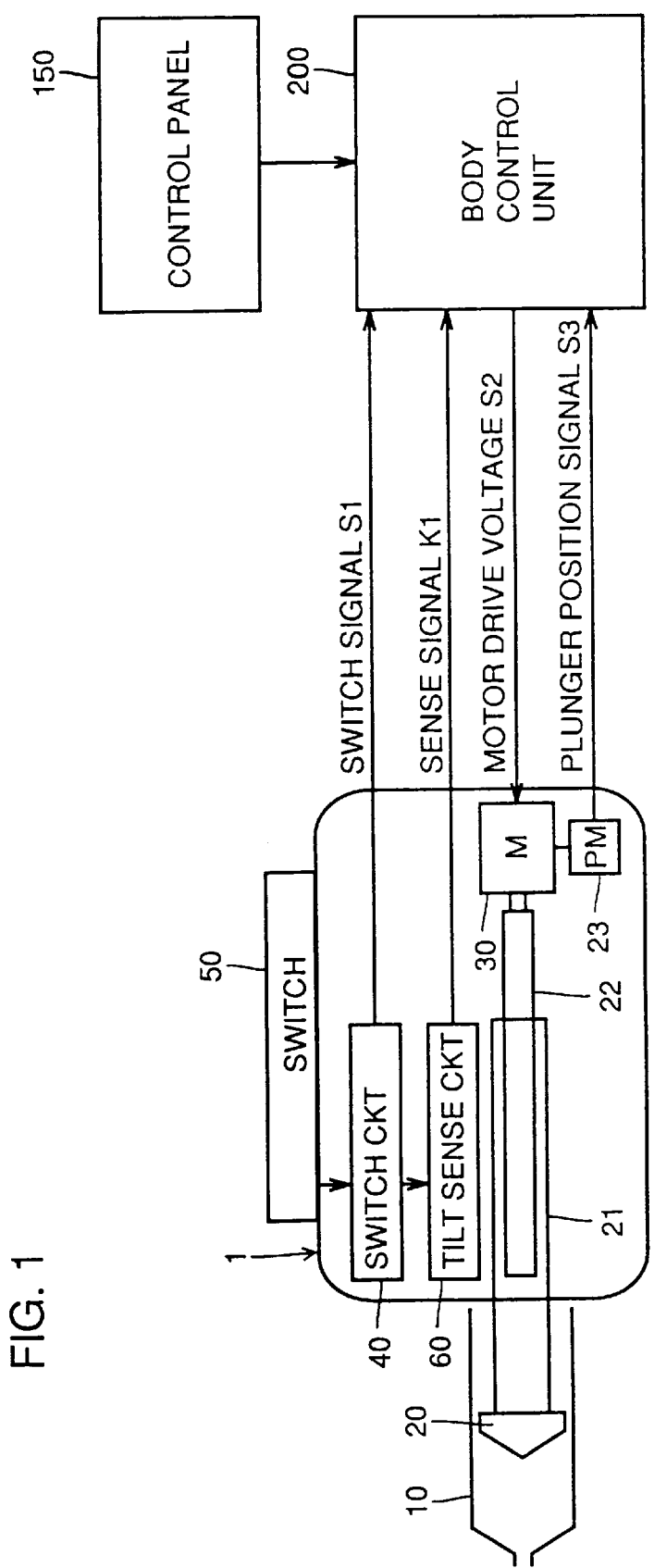
FIG. 1 is a block diagram illustrating a structure of an injector head for medical use according to the present invention.
Figure 2:
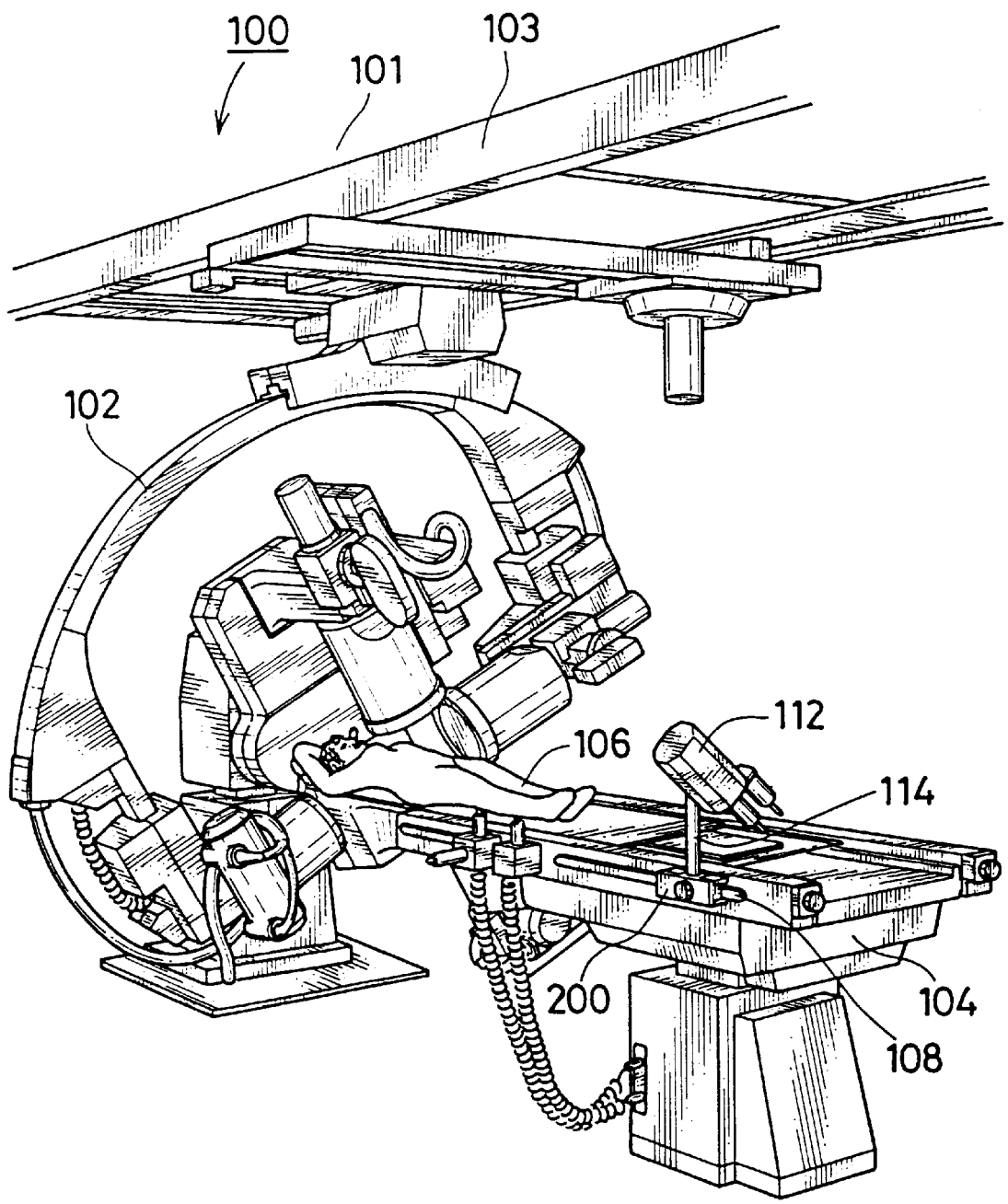
FIG. 2 shows an entire structure of a circulatory organ x-ray diagnostic apparatus.
Figure 3A:
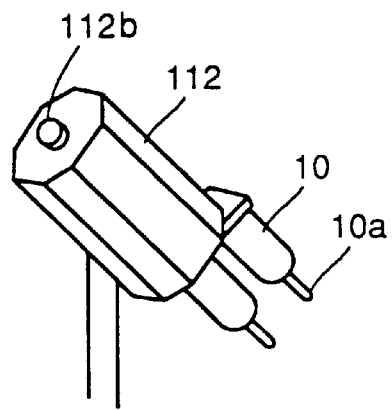
FIGS. 3A and 3B show the injector head for medical use tilting downward and upward respectively.
Figure 3B:
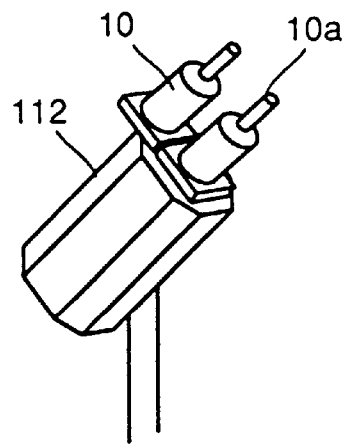
Figure 4:
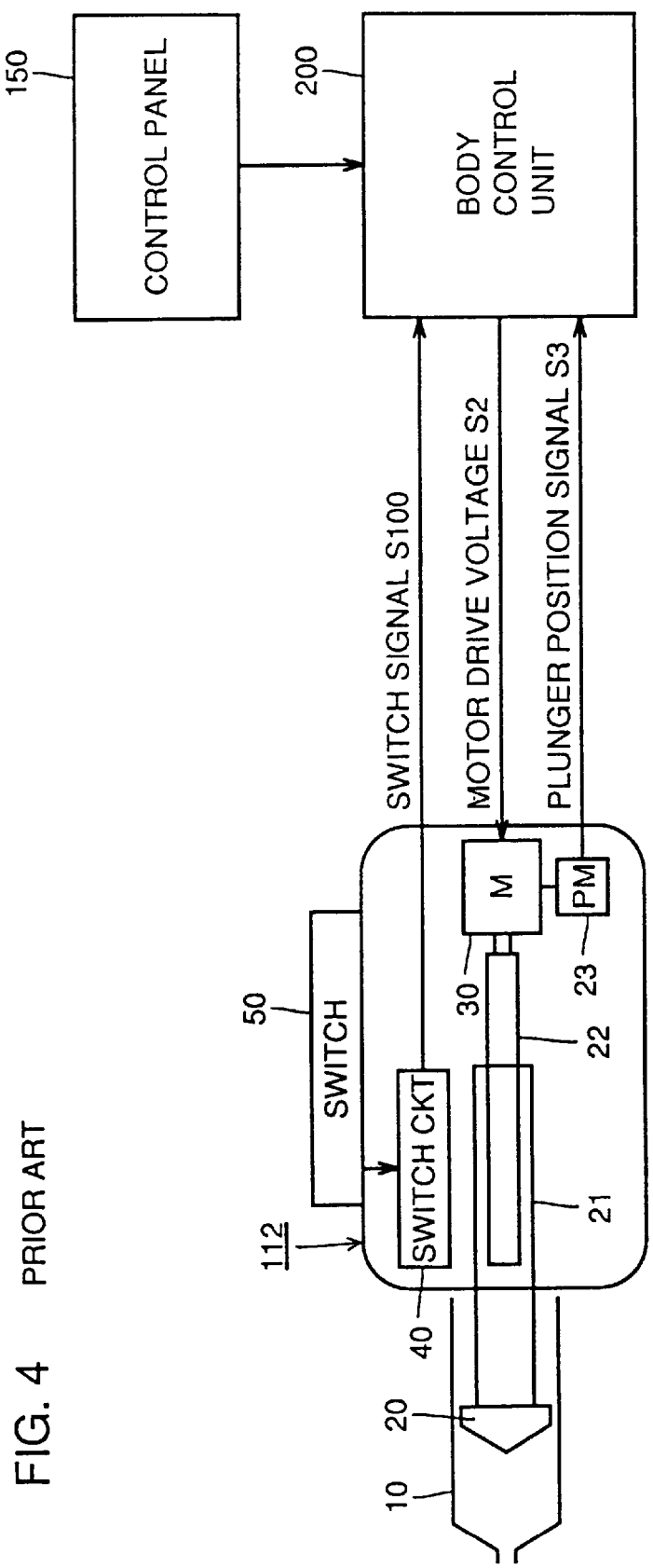
FIG. 4 is a block diagram illustrating a structure of a conventional injector head for medical use.

With reference to FIG. 1, one embodiment of an injector head for medical use according to the present invention will be described.

An injector head for medical use 1 according to this embodiment includes a plunger 21 jointed to a piston 20 provided in a syringe 10. Rotation of a motor 30 is propagated to a ball screw 22, and plunger 21 can be moved forward and backward by ball screw 22.

A potentiometer 23 for sensing a position of plunger 21 is provided for motor 30, and a plunger position signal S3 is output from potentiometer 23 to a body control unit 200. Plunger 21, ball screw 22, motor 30, and potentiometer 23 constitute a piston drive apparatus.

From body control unit 200, a motor drive voltage S2 is output to motor 30. When an amount of injection of contrast medium into a patient is input to a control panel 150, a corresponding signal is output from control panel 150 to body control unit 200, and motor drive voltage S2 is output from body control unit 200 to motor 30. Plunger position signal S3 is output from potentiometer 23 to body control unit 200 as a feedback signal, thereby allowing injection of a highly accurate amount of contrast medium into a patient. Control panel 150 and body control unit 200 constitute a control apparatus.

Injector head for medical use 1 is further provided with a switch 50 for advancing and retracting plunger 21 by manual operation. A variable forward/reverse switch capable of varying speed at moving forward and backward by changing the position on the switch to be pressed is employed as switch 50.

A signal output from switch 50 is supplied to a switch circuit 40 and a switch signal S1 is output from switch circuit 40 to body control unit 200, and motor drive voltage S2 is output from body control unit 200 to motor 30.

The injector head for medical use according to this embodiment is further provided with a tilt sense circuit 60 between switch circuit 40 and body control unit 200 for sensing a tilt of medical injector head 1 and outputting a prescribed sense signal K1 to body control unit 200 based on a prescribed signal output from switch circuit 40. Switch circuit 40, switch 50 and tilt sense circuit 60 constitute an operation apparatus.

Various well-known arts can be applied to means for sensing the tilt of medical injector head 1, provided in tilt sense circuit 60. The tilt of medical injector head 1 can be sensed easily by utilizing a mercury switch, a limit switch utilizing an axis for rotatably supporting medical injector head 1, and an optical switch.

Tilt sense circuit 60 is thus provided for sensing the tilt of medical injector head 1 and outputting prescribed sense signal K1 to body control unit 200 based on a prescribed signal output from switch circuit 40. Accordingly, if medical injector head 1 inclines upward, a signal output from switch circuit 40 is not converted, while if medical injector head 1 inclines downward, the signal output from switch circuit 40 is converted at tilt sense circuit 60 and a prescribed signal K1 is output to body control unit 200.

As a result, when medical injector head 1 tilts downward, plunger 21 can be moved at lower speed by lowering the signal output from switch circuit 40 by conversion even through a normal manual operation using switch 50. Accordingly, when the contrast medium is injected into patient 106 with medical injector head 1 tilting downward, the contrast medium can be sucked without care in order to check if the catheter is surely inserted into the blood vessel of patient 106.

An injector head for medical use can thus be provided which is significantly easy for an operator of the medical injector head to use. As a result, the labor of nurses and medical technologists can be saved.

According to the embodiment described above, a signal output from the switch circuit is converted such that the signal is lowered only when the medical injector head tilts downward. However, when the medical injector head tilts upward or downward, the signal output from switch circuit can be converted for other purposes. For example, a standby state may be set when the injector head for medical use tilts.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An injector head for medical use to which a syringe is attached, the syringe having a cylindrical body portion, injection portion and opening portion respectively at front and rear ends of said cylindrical body portion, the syringe further having a piston arranged movable between the front and rear ends of said body portion for defining an internal space within said body portion for enclosing contrast medium which is to be injected into a patient comprising:

piston drive means for moving said piston toward front end side or rear end side;

control means for inputting/outputting a prescribed control signal into/from said piston drive means; and operation means for inputting a prescribed operation signal to said control means in order to move said piston by manual operation, the injector head further including tilt sense means for sensing a tilt of said injector head for medical use and outputting a sense signal based on the sensing to said control means, wherein a signal output from said operation means is input to said tilt sense means, and based on the signal, said sense signal is output from said tilt sense means to said control means.

2. An injector head for medical use to which a syringe is attached, the syringe having a cylindrical body portion, injection portion and opening portion respectively at front and rear ends of said cylindrical body portion, the syringe further having a piston arranged movable between the front and rear ends of said body portion for defining an internal space within said body portion for enclosing contrast medium which is to be injected into a patient, comprising:

piston drive means for moving said piston toward front end side or rear end side;

control means for inputting/outputting a prescribed control signal into/from said piston drive means; and operation means for inputting a prescribed operation signal to said control means in order to move said piston by manual operation, the injector head further including tilt sense means for sensing a tilt of said injector head for medical use and outputting a sense signal based on the sensing to said control means, wherein when said injector head for medical use tilts upward, a signal output from said operation means is not converted and said sense signal is output from said tilt sense means to said control means and when said injector head for medical use tilts downward, a signal output from said operation means is converted at said tilt sense means and a prescribed sense signal is output to said control means.

3. An injector head for medical use to which a syringe is attached, the syringe having a cylindrical body portion, injection portion and opening portion respectively at front and rear ends of said cylindrical body portion, the syringe further having a piston arranged movable between the front and rear ends of said body portion for defining an internal space within said body portion for enclosing contrast medium which is to be injected into a patient, comprising:

piston drive means for moving said piston toward front end side or rear end side;

control means for inputting/outputting a prescribed control signal into/from said piston drive means; and operation means for inputting a prescribed operation signal to said control means in order to move said piston by manual operation, the injector head further including tilt sense means for sensing a tilt of said injector head for medical use and outputting a sense signal based on the sensing to said control means, wherein a standby signal is output from said tilt sense means to said control means when said injector head for medical use tilts downward.

* * * * *